US007942782B2

(12) United States Patent
Al-Tawil

(10) Patent No.: US 7,942,782 B2
(45) Date of Patent: May 17, 2011

(54) METHODS AND SYSTEMS FOR LINGUAL MOVEMENT TO MANIPULATE AN OBJECT

(76) Inventor: Youhanna Al-Tawil, Knoxville, TN (US)

( * ) Notice: Subject to any disclaimer, the term of this patent is extended or adjusted under 35 U.S.C. 154(b) by 58 days.

(21) Appl. No.: 12/556,237

(22) Filed: Sep. 9, 2009

(65) Prior Publication Data
US 2010/0069200 A1 Mar. 18, 2010

Related U.S. Application Data

(60) Provisional application No. 61/096,408, filed on Sep. 12, 2008.

(51) Int. Cl.
*A63B 71/00* (2006.01)
(52) U.S. Cl. ............... 482/1; 482/11; 600/587; 600/590
(58) Field of Classification Search ............... 482/1–11, 482/900–902; 701/1; 600/587–590, 23; 434/185, 247
See application file for complete search history.

(56) References Cited

U.S. PATENT DOCUMENTS

| | | | |
|---|---|---|---|
| 4,408,192 A | 10/1983 | Ward et al. | |
| 4,562,432 A | 12/1985 | Sremac | |
| 4,567,479 A | 1/1986 | Boyd | |
| 4,629,424 A | 12/1986 | Lauks et al. | |
| 4,697,601 A | 10/1987 | Durkee et al. | |
| 4,746,913 A | 5/1988 | Volta | |
| 4,758,829 A | 7/1988 | Smith | |
| 4,783,656 A | 11/1988 | Katz et al. | |
| 4,865,610 A * | 9/1989 | Muller ........................... 623/24 |
| 4,997,182 A | 3/1991 | Kussick | |
| 5,212,476 A | 5/1993 | Maloney | |
| 5,213,553 A | 5/1993 | Light | |
| 5,422,640 A | 6/1995 | Haley | |
| 5,452,727 A | 9/1995 | Tura et al. | |
| 5,460,186 A * | 10/1995 | Buchhold ................ 340/825.19 |
| 5,523,745 A | 6/1996 | Fortune et al. | |
| 5,609,161 A | 3/1997 | Tura et al. | |
| 5,689,246 A | 11/1997 | Dordick et al. | |
| 5,830,235 A | 11/1998 | Standley | |

(Continued)

OTHER PUBLICATIONS

Pressure Sensor article, http://en.wikipedia.org/wiki/Pressure_sensor (4 pages).

(Continued)

*Primary Examiner* — Glenn Richman
(74) *Attorney, Agent, or Firm* — Peter L. Brewer; Baker, Donelson, Bearman, Caldwell & Berkowitz, PC

(57) ABSTRACT

An intra-oral system is disclosed for assisting an individual in developing intra-oral muscle control and strength. The system may also be used to enable an individual having limited use of the upper extremities to control an electrical apparatus such as a wheelchair, a bed or a light fixture. The intra-oral system includes a mouthpiece having a plurality of air cells embedded therein. The air cells are configured to receive pressure applied by the tongue of an individual. Movement of the tongue over and against the air cells causes an object to be moved over a display. In one embodiment, the object is moved through an obstacle course or over a simulated track as part of a therapeutic regimen. In another embodiment, a character or icon on the display is selected and activated to manipulate an electrical apparatus. Methods for moving an electrical apparatus using a mouthpiece controlled through lingual movement are also provided.

53 Claims, 7 Drawing Sheets

U.S. PATENT DOCUMENTS

| | | | |
|---|---|---|---|
| 5,904,140 A | 5/1999 | McGoogan | |
| 5,954,673 A | 9/1999 | Staehlin et al. | |
| 6,033,367 A | 3/2000 | Goldfield | |
| 6,050,961 A | 4/2000 | Arnold | |
| 6,108,592 A | 8/2000 | Kurtzberg et al. | |
| 6,190,335 B1 | 2/2001 | Howard et al. | |
| 6,222,524 B1 | 4/2001 | Salem et al. | |
| 6,430,450 B1 | 8/2002 | Bach-y-Rita et al. | |
| 6,511,441 B1 | 1/2003 | Wakumoto et al. | |
| 6,702,765 B2 | 3/2004 | Robbins et al. | |
| 6,801,231 B1 | 10/2004 | Beltz | |
| 6,893,406 B2 | 5/2005 | Takeuchi et al. | |
| 6,897,788 B2 | 5/2005 | Khair et al. | |
| 6,971,993 B2 | 12/2005 | Fletcher | |
| 7,127,270 B2 * | 10/2006 | Sinclair | 455/556.1 |

OTHER PUBLICATIONS

Y. Takahashi, et al., High-speed Pressure Sensor Grid for Humanoid Robot Foot, IEEE/IROS (2005).

Pressure Mapping Systems article, http://www.sensorland.com/HowPage033.html (May 22, 2008) (7 pages).

Pressure Transducers article, http://www.omega.com/prodinfo/pressuretransducers.html (May 27, 2008) (3 pages).

Piezoelectric sensor article, http://en.wikipedia.org/wiki/Piezoelectric_sensor (May 27, 2008) (5 pages).

ASDX Sensors brochure, www.honeywell.com/sensing (Sep. 28, 2009) (4 pages).

FlexiForce specifications, Tekscan, Rev F_062408 (1 page).

Sealtech services brochure, Athens, Tennessee (8 pages).

Adult Pacifier article, http://www.diaperconnection.com/pacifier.html (Sep. 28, 2009) (3 pages).

* cited by examiner

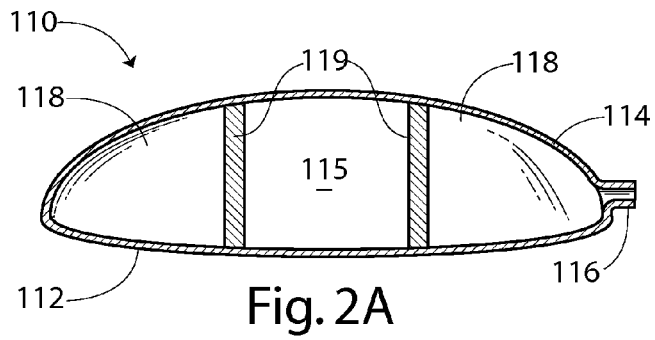
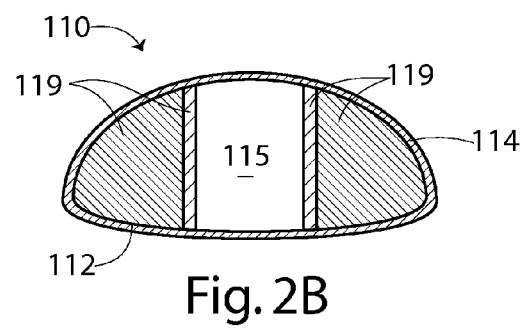
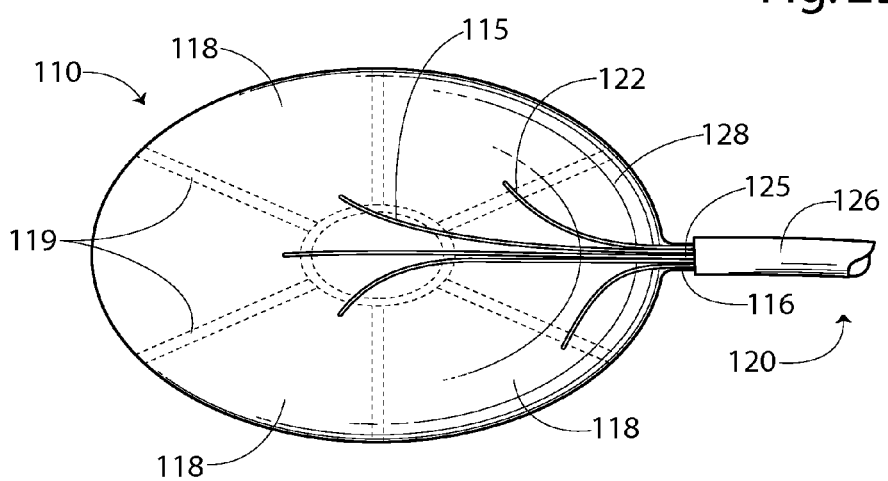
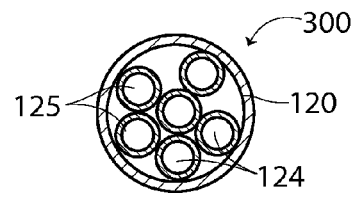

METHODS AND SYSTEMS FOR LINGUAL MOVEMENT TO MANIPULATE AN OBJECT

CROSS REFERENCE TO RELATED APPLICATIONS

This application claims the benefit of a provisional patent application bearing U.S. Ser. No. 61/096,408, filed Sep. 12, 2008. That application is entitled "Methods and Systems for Improving Mastication and Deglutition." The provisional patent application is incorporated herein by reference in its entirety.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

BACKGROUND OF THE INVENTION

1. Field of the Invention

The present invention relates to therapeutic devices. More specifically, the present invention relates to methods and systems for helping patients improve mastication and deglutition. The present invention also has application to the movement of an object on a visual display in order to activate an electrical apparatus.

2. Technology in the Field of the Invention

Mastication, or chewing, is the process by which food is mashed and crushed by teeth. Mastication increases the surface area of food and allows it to more efficiently be broken down by enzymes. This is the first step of digestion.

During the mastication process, food is positioned between the teeth for grinding by the cheek and tongue. As chewing continues, the food is made softer and warmer. Enzymes in the saliva begin to break down carbohydrates in the food. After chewing, the food (now called "bolus") is swallowed. It enters the esophagus and continues on to the stomach where the next step of digestion occurs.

Many foods require at least some chewing for proper digestion. However, some individuals lack the muscular ability to grind food with their tongue and teeth. Physical difficulty in chewing food may arise in young patients due to a neurological or muscular birth defect. Alternatively, such a difficulty may arise in older patients due to a partial stroke or injury. Such individuals are thus limited in what they can eat.

There are also some individuals who have trouble swallowing food and saliva. All food and saliva must be swallowed. Patients who lack the muscular ability to swallow food also cannot eat properly. Such a condition is referred to as dysphagia.

Deglutition, or swallowing, is the complex process by which food and saliva are moved from the mouth, through the pharynx, and into the stomach. Both food and air pass through the pharynx, a part of the neck and throat positioned immediately posterior to the mouth and the nasal cavity, superior to the larynx, esophagus, and trachea. In other words, the pharynx (along with the esophagus and larynx), is part of both the respiratory system and digestive system in humans.

Deglutition is actually a two phase process involving both the somatic (voluntary) and autonomic (involuntary) nervous systems. For swallowing, the voluntary phase is referred to as the buccal phase, while the involuntary phase occurs as food is moved from the oral cavity into the pharynx.

Concerning the buccal phase, this phase occurs when a bolus, a soft mass of sufficiently chewed food mixed with saliva, is transferred to the back of the tongue. The anterior portion of the tongue lifts toward the hard palate in the mouth and then descends backwards to force the bolus into the pharynx. Next, the posterior portion of the tongue lifts toward the soft palate, elevating the uvula to seal off the nasopharynx. This prevents the bolus from entering the nasal cavity. The buccal phase involves cranial nerves V, VII, and XII, and is controlled by the somatic nervous system.

Once the bolus has entered the pharynx, receptors trigger an involuntary response by the deglutition center in the brain. This pharyngeal-esophageal phase involves cranial nerves V, IX, X, XI, and XII. Pharyngeal folds on either side of the bolus are drawn together to create a narrow passageway. The bolus is forced through the pharynx by peristalsis, which is a series of involuntary muscle contractions. At the same time, the hyoid bone and larynx move upward and forward. This causes the epiglottis to swing backwards, where it blocks the opening to the larynx. The bolus can now pass only into the esophagus; all other openings have been blocked. The esophageal sphincter relaxes, allowing the bolus to enter.

During the brief time that the larynx is sealed off, the swallowing center directly inhibits the respiratory center, halting respiration. Once the bolus enters the esophagus, peristalsis continues to force the food onward toward the stomach while the pharynx returns to its resting state. This is the involuntary process which occurs once food enters the pharynx.

During respiration, air travels from the oral or nasal cavity into the pharynx and then on through the larynx to the trachea and lungs. When food is swallowed, it travels from the oral cavity into the pharynx, and then into the esophagus. During swallowing, a flap of tissue called the epiglottis (part of the larynx) folds down to direct food away from the trachea and into the esophagus, thus preventing aspiration of food into the lungs. Faulty chewing or swallowing may lead to malnutrition, dehydration, airway obstruction (choking), aspiration pneumonia, and even death.

Dysphagia may arise in young patients due to a neurological or muscular birth defect. Alternatively, it may arise in older patients due to a partial stroke or loss of muscle strength. If the muscles of the tongue or cheek are weak or are not functioning properly, it may be difficult to move food around in the mouth for proper chewing. Food pieces that are not chewed properly may be too large to swallow and can block the passage of air when they enter the throat.

A need exists for a device that assists patients in strengthening the intra-oral musculature and in improving muscular control in connection with mastication and deglutition. A need further exists for a system by which a patient's ability to chew and swallow food may be improved by means of muscle therapy and visual feedback. A need further exists for an intra-oral system by which an individual may control an object on a visual display for activating an electrical apparatus.

BRIEF SUMMARY OF THE INVENTION

An intra-oral system is first provided. In one application, the system is beneficial for assisting an individual in developing intra-oral muscle control and strength. This, in turn, assists the patient in deglutition and mastication. The individual may be a patient undergoing therapy.

In another application, the system may be used by an individual who is significantly impaired in the use of his or her upper extremities. The system enables this individual to move an object on a visual display. Using the visual display, this individual may actuate an electrical apparatus. Further, this individual may "type" a message on a digital keyboard.

In one embodiment, the intra-oral system includes a mouthpiece. The mouthpiece includes a bulb fabricated from an elastomeric material. Examples of elastomeric materials include polyisoprene rubber, silicon, chloroprene rubber, neoprene, styrene butadiene rubber, acrylonitrile butadiene rubber, ethylene propylene diene methylene, polyvinylchloride, polyethylene, polyurethane, urethane-coated nylon, ethyl vinyl acetate, and combinations thereof.

The mouthpiece has a plurality of air cells embedded therein. The air cells are configured to receive pressure applied by the tongue of an individual. In one embodiment, the mouthpiece comprises at least three outer or radial air cells, with the air cells being disposed radially around a centerpoint. The centerpoint may simply be a geographical point of centricity, or it may define a separate air cell. The air cells are separated by walls fabricated within the mouthpiece.

The intra-oral system also includes a plurality of air tubes. Each air tube has a proximal end and a distal end. The distal end of each of the air tubes is in substantially sealed fluid communication with a corresponding air cell. This may be by means of an integral connection between the distal end of the air tubes and respective walls. Each of the plurality of air tubes may generally reside at ambient pressure. Alternatively, and by way of example, each of the plurality of air tubes may be pre-loaded at a pressure of about 15 psi to 25 psi.

A plurality of transducers is also provided as part of the intra-oral system. Each transducer is in substantially sealed fluid communication with the proximal end of a corresponding air tube. The transducers convert changes in air pressure within the respective air cells to corresponding electrical signals. Such electrical signals may be, for example, voltage signals, current signals, or resistive changes. The transducers are preferably in the nature of pressure sensors.

The intra-oral system also includes a processor. The processor serves to process the electrical signals. The electrical signals, such as voltage signals, are modulated to generate a pressure profile from the air cells. The pressure profile represents a magnitude of pressure within the air cells, a direction of pressure, a duration of pressure, or combinations thereof.

The processor is controlled by an algorithm, which in turn is written to perform a designated operation. In one aspect, the operation relates to the movement of an object through an obstacle course. In this context, the intra-oral system may be used by a patient for therapy. In another aspect, the function relates to the movement of a cursor across a keyboard. The keyboard will have alphanumeric or other characters. In this context, the intra-oral system may be used by a patient or other individual to move the cursor to, for example, control the direction and movement of a wheelchair or to activate or deactivate apparatus' or other electrical objects.

The intra-oral system also includes a display. The display is in electrical communication with the processor. The display provides a visual output to move an object in accordance with the pressure profile. The object is manipulated by application of pressure on the air cells by lingual movement.

The pressure profile is based upon pressure readings from the various air cells. In one aspect, air pressure signals are processed such that:

each electrical signal represents an air pressure reading from a corresponding air cell; and electrical signals associated with one or more corresponding air cells are averaged over a specified period of time to produce the pressure profile, the pressure profile having a peak indicative of location at which air pressure is being generated within the one or more air cells during the specified period of time.

In one aspect, a magnitude of each electrical signal is recorded as part of the pressure profile over the specified period of time. The object is then caused to be moved on the display in the direction indicated by the pressure profile at a velocity that generally corresponds to the magnitude of the electrical signals. In another aspect, an application of pressure by a patient on the centerpoint for a specified period of time and at a specified magnitude causes a location of the object to be reset to a beginning point on the display. Alternatively, an application of pressure by a patient on a designated radial air cell for a specified period of time and at a specified magnitude causes a location of the object to be moved to a corresponding location on the display.

In another aspect, an application of pressure by a patient on the centerpoint for a specified period of time and at a specified magnitude causes the object to jump over an obstacle on the display or to activate or deactivate an appliance or other electrical object. Alternatively, a double-clicking of application of pressure by a patient on the centerpoint for a specified period of time and at a specified magnitude causes a location of the object to be reset to a beginning point on the display, or causes the object to jump over an obstacle on the display.

A method for improving intra-oral motor skills of a patient is also provided herein. In one embodiment, the method includes providing an intra-oral system. The intra-oral system is generally designed as described above. In this respect, the system has a mouthpiece that defines an elastomeric bulb. The bulb has a plurality of air cells embedded therein for receiving pressure applied by the tongue of a patient.

The intra-oral system also includes a plurality of air tubes. The distal end of each of the air tubes is in substantially sealed fluid communication with a corresponding air cell. The intra-oral system further includes a plurality of transducers. The transducers convert changes in air pressure within the air cells to electrical signals.

The intra-oral system also includes a processor for processing the electrical signals. The electrical signals, such as voltage signals, are modulated to generate a pressure profile from the air cells. The pressure profile represents a magnitude of pressure within the air cells at a particular time, a direction of pressure, a duration of pressure, or combinations thereof.

The pressure profile is based upon pressure readings from the various air cells. In one aspect, air pressure signals are processed such that each electrical signal represents an air pressure reading from a corresponding air cell. Electrical signals from one or more corresponding air cells are averaged over a specified period of time to produce the pressure profile. The pressure profile has a peak indicative of location at which air pressure is being generated within the one or more air cells during the specified period of time.

The intra-oral system also includes a display. The display is in electrical communication with the processor. The display has a visual output to move an object in accordance with the pressure profile. The method then also includes the steps of placing the plurality of air tubes in fluid communication with the corresponding plurality of transducers, and placing the processor in electrical communication with the display.

The method next includes causing an object on the display to move in accordance with the pressure profile. This is done by means of lingual manipulation, meaning that the user applies pressure to the air cells using their tongue.

The user may be, for example, a patient who is in therapy. Here, the object is moved by the patient as part of therapy. Movement of the object helps the patient develop intra-oral muscle strength and coordination for mastication and deglutition. Alternatively, a user may be an individual who has limited mobility or dexterity in their upper extremities. The object is moved by the user to operate a wheelchair or a bed.

In one aspect, a magnitude of each electrical signal is recorded as part of the pressure profile over the specified period of time. The object is then caused to be moved on a display in the direction indicated by the pressure profile at a velocity that corresponds to the magnitude of the electrical signals. In another aspect, an application of pressure by a patient on the centerpoint for a specified period of time and at a specified magnitude causes a location of the object to be reset to a beginning point on the display. Alternatively, an application of pressure by a patient on a designated outer air cell for a specified period of time and at a specified magnitude causes a location of the object to be moved to a corresponding location on the display.

Finally, a method for manipulating an electrical apparatus using lingual musculature is also provided herein. In one embodiment, the method includes providing an intra-oral system. The intra-oral system is generally designed as described above. In this respect, the system has a mouthpiece that defines an elastomeric bulb. The bulb has a plurality of air cells embedded therein for receiving pressure applied by the tongue of a patient.

The intra-oral system also includes a plurality of air tubes. In one embodiment, each of the plurality of air tubes resides substantially at ambient pressure. Alternatively, the air tubes may be pre-loaded to a pressure of about 15 psi to 25 psi. The air tubes preferably have an inner diameter of about 0.05 inches to 0.5 inches.

The distal end of each of the air tubes is in substantially sealed fluid communication with a corresponding air cell. The intra-oral system further includes a plurality of transducers. The transducers convert changes in air pressure within the air cells to electrical signals. Changes in air pressure are communicated to the transducers by means of the air tubes.

The intra-oral system will also include a processor for processing the electrical signals. These may be, for example, analog signals. The electrical signals are modulated to generate a pressure profile from the air cells.

The pressure profile is based upon pressure readings from the various air cells. In one aspect, air pressure signals are processed such that each electrical signal represents an air pressure reading from a corresponding air cell. Electrical signals from one or more corresponding air cells are averaged over a specified period of time to produce the pressure profile. The pressure profile has a peak indicative of location at which air pressure is being generated within the one or more air cells during the specified period of time.

The intra-oral system also includes a display. The display is in electrical communication with the processor. The display has a visual output to move an object in accordance with the pressure profile.

The method also includes the steps of placing the plurality of air tubes in fluid communication with the corresponding plurality of transducers, and placing the processor in electrical communication with the display. The display, again, has a visual output. The method then includes causing an object on the display to move in accordance with the pressure profile.

In one aspect, a magnitude of each electrical signal is recorded as part of the pressure profile over the specified period of time. The object is then caused to be moved on a display in the direction indicated by the pressure profile at a velocity that corresponds to the magnitude of the electrical signals. In another aspect, an application of pressure by a patient on the centerpoint for a specified period of time and at a specified magnitude causes a location of the object to be reset to a beginning point on the display. Alternatively, an application of pressure by a patient on a designated outer air cell for a specified period of time and at a specified magnitude causes a location of the object to be moved to a corresponding location on the display.

In accordance with this method of manipulating an electrical apparatus using lingual musculature, a symbol is clicked. The symbol on the display may be of any type. For example, the symbol may be a picture. Alternatively, the symbol may be one or more alphanumeric characters, an arrow, a picture (or icon), or a geometric figure. Using their tongue, the user clicks on a symbol on the display to activate (or move) an electrical apparatus. The electrical apparatus may be a wheelchair. Alternatively, the electrical apparatus may be, for example, a television, a light fixture or an electro-mechanically operated door.

In one aspect, the mouthpiece comprises at least three outer air cells disposed radially around a centerpoint. The centerpoint may define a separate air cell in fluid communication with one of the plurality of air tubes.

In one aspect, the signal processor receives voltage signals from each of the plurality of transducers. The processor then processes the signals such that:

each voltage signal represents an air pressure reading from a corresponding air cell; and voltage signals from one or more corresponding air cells are averaged over a specified period of time to produce the pressure profile, the pressure profile having a peak indicative of location at which air pressure is being generated within the one or more air cells during the specified period of time.

BRIEF DESCRIPTION OF THE DRAWINGS

So that the manner in which the present invention can be better understood, certain illustrations, charts and/or flow charts are appended hereto. It is to be noted, however, that the drawings illustrate only selected embodiments of the inventions and are therefore not to be considered limiting of scope, for the inventions may admit to other equally effective embodiments and applications.

FIG. 2A is a cross-sectional view of the mouthpiece from the system of FIG. 1, in one embodiment. The cross-section is taken across a major axis of the mouthpiece.

FIG. 2B is another cross-sectional view of the mouthpiece from the system of FIG. 1. Here, the cross-section is taken across a minor axis of the mouthpiece.

FIG. 2C is a top view of the mouthpiece from the system of FIG. 1. Individual air cells are shown along with corresponding air tubes.

FIG. 3 is a cross-sectional view of the air tube bundle from the system of FIG. 1, in one embodiment.

In FIG. 4A, the display shows an object that is being moved through an obstacle course. The object is moved through lingual manipulation.

In FIG. 4B, the display shows directional keys for moving a wheelchair or a bed. The keys are activated by using a cursor that is moved through lingual manipulation.

In FIG. 4C, the display shows a keyboard and icons for various electrical apparatus' that may be operated using a cursor that is moved through lingual manipulation.

DETAILED DESCRIPTION OF CERTAIN EMBODIMENTS

Figure 1:
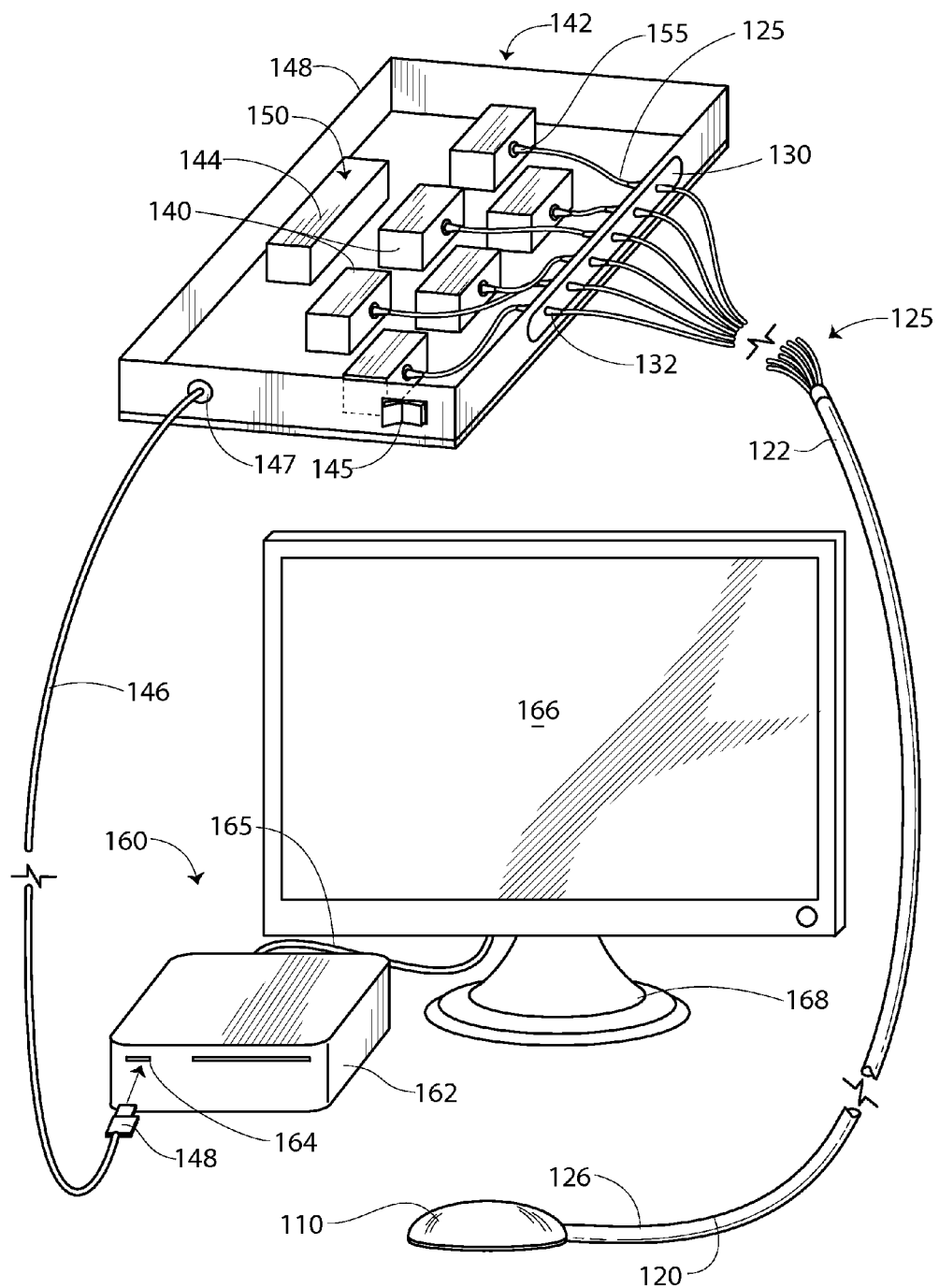
FIG. 1 is a perspective view of an intra-oral system according to the present invention, in one embodiment.

FIG. 1 is a perspective view of an intra-oral system 100 according to the present invention, in one embodiment.

The intra-oral system 100 first includes a mouthpiece 110. The mouthpiece 110 is configured to be selectively inserted into an individual's mouth (not shown). The individual may be a patient who is in need of therapy to develop the intra-oral musculature. Such a patient may be, for example, a stroke victim or the victim of a head or neck injury. Alternatively, such a patient may be a child who suffers from congenital limitations in chewing food and/or swallowing food.

The mouthpiece is preferably fabricated from an elastomeric material. Suitable materials may include polyisoprene rubber, chloroprene rubber, neoprene rubber, styrene butadiene rubber, and acrylonitrile butadiene rubber. Additional suitable examples include silicon, ethylene propylene diene methylene, polyvinylchloride, polyethylene, polyurethane, urethane-coated nylon, and ethyl vinyl acetate. Combinations of these materials may also be employed.

Enlarged drawings of the mouthpiece 110 are provided in FIGS. 2A-2C. FIG. 2A is a cross-sectional view of the mouthpiece 110 from the system of FIG. 1, in one embodiment. The cross-section is taken across a major axis. FIG. 2B is another cross-sectional view of the mouthpiece 110 from the system of FIG. 1. Here, the cross-section is taken across a minor axis. FIG. 2C is a top view of the mouthpiece 110 from the system of FIG. 1. Features of the mouthpiece 110 will be discussed with reference to these three figures together.

The mouthpiece 110 is designed to be substantially hollow. To this end, the mouthpiece 110 defines a bottom surface 112 and a top surface 114. The bottom surface 112 is preferably substantially flat while the top surface 114 is preferably curved to create an arcuate profile. Thus, the mouthpiece 110 is in the nature of a bulb.

The mouthpiece 110 also includes a plurality of air cells 115, 118. In the arrangement of FIGS. 2A-2C, six air cells 115, 118 are provided. These represent a central air cell 115 and then separate air cells 118 spaced radially around the central air cell 115. Preferably, at least three radial air cells 118 are provided. In the illustrative arrangement of FIGS. 2A-2C, the mouthpiece 110 has five radial air cells 118. The radial air cells 118 preferably are equi-radial in dimension, meaning that each air cell 118 forms a substantially equal angle extending from a center point of the mouthpiece 110.

Each air cell 115, 118 holds a volume of air. Preferably, the air is held at ambient pressure. Alternatively, the air in the air cells 115, 118 is pre-loaded at a higher pressure such as between about 15 psi and 25 psi. In this way, the mouthpiece 110 is resistive to pressure placed by the patient using his or her tongue.

To define the air cells 115, 118, the mouthpiece 110 includes a series of walls 119. The walls 119 are sealed between the bottom surface 112 and the top surface 114. Sealing may be through heat sealing, RF sealing, or other mechanisms known in the art of plastic injection molding or other molding techniques.

The mouthpiece 110 may be configured in different sizes. The size will primarily be dictated by the size of the individual user's mouth. It is noted that for smaller patients, fewer air cells may be required due to size limitations.

The intra-oral system 100 also includes a plurality of air tubes 125. An air tube 125 is provided to correspond to each radial air cell 118. Optionally, an air tube 125 is also provided for the central air cell 115. The air tubes 125 are sealingly disposed within the walls 119 of the mouthpiece 110. The air tubes 125 are preferably manufactured to be integral to respective walls 119.

It is noted that in the mouthpiece 110 of FIG. 2C, the central air cell 115 receives an air tube 125. However, in some embodiments the central air cell may be dead, meaning that it does not receive its own air tube 125. Indeed, in another arrangement, the central air cell 115 holds no air, but just defines a center point in the mouthpiece 110.

The air tubes 125 exit the mouthpiece 110 through an end opening 116. The end opening 116 defines a circular orifice that frictionally receives a bundle of air tubes 125. The air tubes 125 extend from respective walls 119, travel through an end area 128 of the mouthpiece 110 (which is not an air cell), travel through the end opening 116, and then exit the mouthpiece 110.

In the mouthpiece 110 of FIG. 2C, the air tubes 125 connect to the walls 119 internal to the mouthpiece 110, that is, through the end area 128 and through the central air cell 115. However, some or all of the air tubes 125 may alternatively enter the air cells 115, 118 from a top, a bottom or an outer edge of the bulb defining the mouthpiece 110. The present inventions are not limited by the method of providing fluid communication between the air tubes 125 and the air cells 115, 118 unless so provided in the claims.

In the arrangement of FIG. 1, the air tubes 125 are bundled as they exit the mouthpiece 110. That means that the air tubes 125 are held together externally by a tubular sheath 120.

FIG. 3 is a cross-sectional view of an air tube bundle 300 from the system of FIG. 1, in one embodiment. In the arrangement of FIG. 3, the air tube bundle 300 includes a tubular sheath 120. The tubular sheath 120 helps to protect the air tubes 125 and keeps them from getting punctured or tangled. Six illustrative air tubes 125 are seen within the tubular sheath 120. Each air tube 125 defines an air channel 124 through which air passes. It is understood that any number of air tubes 125 and corresponding air cells 115, 118 may be used in the system 100.

Referring again to FIG. 1, the system 100 also includes a plurality of transducers 140. The transducers 140 are in the nature of pressure sensors. The transducers 140 may be, for example, ASDX pressure sensors made by the Sensing and Control Division of Honeywell in Golden Valley, Minn. The ASDX series of pressure sensors utilize a small internal diaphragm for sensing fine variations in pressure. Different sensors are offered in the series for sensing within different pressure ranges. Such ranges include 0 to 1 psi, 0 to 5 psi, 0 to 15 psi, and 0 to 30 psi. The ASDX sensors offer a high level output (4.0 Vdc span) that is fully calibrated and temperature compensated with on-board Application Specific Integrated Circuitry (ASIC).

The transducers 140 are preferably housed within an operational box 142. The box 142 has walls 148 and a top (not shown). The operational box 142 will include an electrical circuit board 144 that places the transducers 140 in electrical communication with one another as well as with a power supply. A power switch for the operational box 142 is seen at 145.

The transducers 140 are in fluid communication with respective air cells 115, 118. This is done by means of the air tubes 125. A proximal end of each air tube 125 is connected to a transducer 140 at a connection point 155, while a distal end of each air tube 125 is connected to a respective air cell 115, 118, preferably at or through a respective wall 119 in the mouthpiece 110.

Each of the air tubes 125 may extend unbroken from a transducer 140 to an air cell 115 or 118. However, it is preferred that a manifold 130 be provided to enable connections of air tubes 125 inside and outside of the operational box 142. The manifold 130 includes a plurality of prongs 132. Each of the prongs 132 defines a channel that extends from each side of the manifold 130. This means that each prong 132 is actually a pair of prongs, with one prong of a pair of prongs extending inside of the operational box 142, and another prong of the pair of prongs extending outside of the operational box 142. In this way, each pair of prongs 132 enables fluid communication through the air tubes 125 without necessity of the operator opening the box and exposing the delicate transducers 140. Further, the therapist or other operator is not required to manipulate the fragile connection 155 between the air tubes 125 and the respective transducers 140. Preferably, the air tubes 125 are color-coded with the prongs 132 so that the air tubes 125 properly correspond to the correct transducers 140. Alternatively, other coding systems may be used such as alphabetical or numeric associations, or the use of symbols. Alternatively still, custom connectors which connect the air tubes 125 to the prongs 132 in only one orientation may be utilized.

It is noted again that the air tubes 125 are preferably bundled by a tubular sheath 120. The tubular sheath 120 extends generally from the manifold 130 to the end opening 116 of the mouthpiece 110. A proximal end 122 of the tubular sheath 120 begins near the manifold 130, while a distal end 126 of the tubular sheath 120 covers the end opening 116 of the mouthpiece 110. In this way, the mouthpiece 110, the air tubes 125 outside of the operational box 142, and the tubular sheath 120 are essentially one integral unit. Each patient is supplied with his or her own mouthpiece 110 having integrated air tubes 125 and the tubular sheath 120. The only "assembly" required by the therapist is to connect the air tubes 125 with the external prongs 132 on the manifold 130.

The transducers 140 are designed to convert changes in air pressure within the air cells 115, 118 to electrical signals. The electrical signals may be analog voltage signals. Other examples of electrical signals that may be used include current signals or resistive changes. The changes in air pressure within the air cells 115, 118 are delivered pneumatically to the transducers 140 through the respective air tubes 125. As the transducers 140 sense an increase in air pressure, a corresponding voltage or other electrical signal is delivered through the electrical circuit board 144.

The intra-oral system 100 also includes a processor 150. The processor 150 uses operational software for processing the electrical signals. As shown in the arrangement for the system 100 of FIG. 1, the electrical signals are delivered to the processor 150 by means of the electrical circuit board 144. This means that the processor 150 also resides within the operational box 142. However, in another embodiment the processor 150 resides outside of the operational box 142. In yet another arrangement, electrical signals may be sent through a wireless connection such as through use of Bluetooth technology.

In any instance, the electrical signals, such as voltage signals, are modulated to generate a pressure profile from the air cells 115 and/or 118. The pressure profile represents magnitude of pressure within the air cells 115 and/or 118. Alternatively or in addition, the pressure profile represents a location or direction of pressure within the air cells 115 and/or 118. Alternatively or in addition, the pressure profile represents a duration of pressure applied to the air cells 115 and/or 118.

The pressure profile is based upon pressure readings from the various air cells, either individually or through some combination. In one aspect, air pressure signals are processed such that each electrical signal represents an air pressure reading from a corresponding air cell. Electrical signals from one or more corresponding air cells may be averaged over a specified period of time to produce the pressure profile. The pressure profile has a peak indicative of location at which air pressure is being generated within the one or more air cells during the specified period of time.

The pressure profile can be used to determine direction. A curve-fitting technique may be used with the pressure readings of the outside ring of air cells as data points. In one instance, a Gaussian curve-fitting technique is used to determine the peak pressure, yielding a representation of the radial direction from 0 to 360 degrees.

The pressure profile can be used to determine the magnitude of pressure applied by the patient. The preferred method is to use the average value of the pressure profile across all air cells 115, 118 to represent this magnitude. In certain scenarios, the associated pressure value from the central air cell 115 can be solely used to determine the magnitude. A baseline or steady-state value representing no pressure being applied to the mouthpiece 110 may be subtracted from the pressure profile to more accurately determine the actual pressure applied by the patient.

When a pressure profile is generated, a normalization procedure may be used to remove differences in pressure-to-voltage characteristics between air cells. These differences can arise due to manufacturing imperfections in the air cells 115, 118 and/or the electronics. The normalization values can be stored on the processor 150 and/or a computer, seen at 160.

An electrical cord 146 extends from the operational box 142. More specifically, the cord 146 extends from an opening 147 in the operational box 142. The cord 146 preferably has a USB connector 148 for placing the processor 150 in electrical communication with a computer 160. More specifically, the USB connector 148 places the processor 150 in electrical communication with a processing unit 162 for a computer 160.

The computer 160 is preferably a general purpose computer 160. Such a computer may be a laptop computer or a desk top computer as may be purchased at a local retail store. In this instance, communications software may be loaded onto the processing unit 162 by the therapist or IT representative. However, the processing unit 162 may be a specially designed or dedicated unit that comes with the operational box 142. Alternatively, the processing unit 162 may be a central processing unit that is part of a network.

In operation, the system 100 allows a patient to manipulate an object on a screen. This is done by the patient moving his or her tongue across and against the bottom surface 112 of the mouthpiece 110. Such movement causes an increase in air pressure within selected air cells 115, 118. The increase in air pressure causes a corresponding increase in air pressure within the air tubes 125. This, in turn, is transmitted to the respective transducers 140 within the operational box 142.

Electrical signals are generated by the transducers 140 in response to the changes in air pressure within the air tubes 125. These signals are sent to the processor 150. The processor 150, in turn, modulates the signals and sends them to display software residing on the processing unit 162. Using the display or "game" software, an object (not shown in FIG. 1) is caused to be moved across a display 166. Manipulation of the object allows the patient to increase strength within the oral musculature, and to improve lingual dexterity.

To implement this function, the system 100 also includes the visual display 166. The display 166 represents a screen for visualizing the object as it is moved by the patient. The display 166 may include a stand 168 for supporting the display 166. Preferably, the display 166 is adjustable to accommodate the height or position of the patient. A cord 165 is offered to provide the needed electrical communication between the processing unit 162 and the display 166 when the two are not part of an integral device such as a laptop computer.

It is understood that the display 166 arrangement of FIG. 1 is merely illustrative. The display 166 may be part of a laptop computer. Alternatively, the display 166 may be part of a headset, or may comprise a large, wall-mounted screen. Alternatively still, the display 166 may be a screen that receives an image from a projector.

Figure 4A:
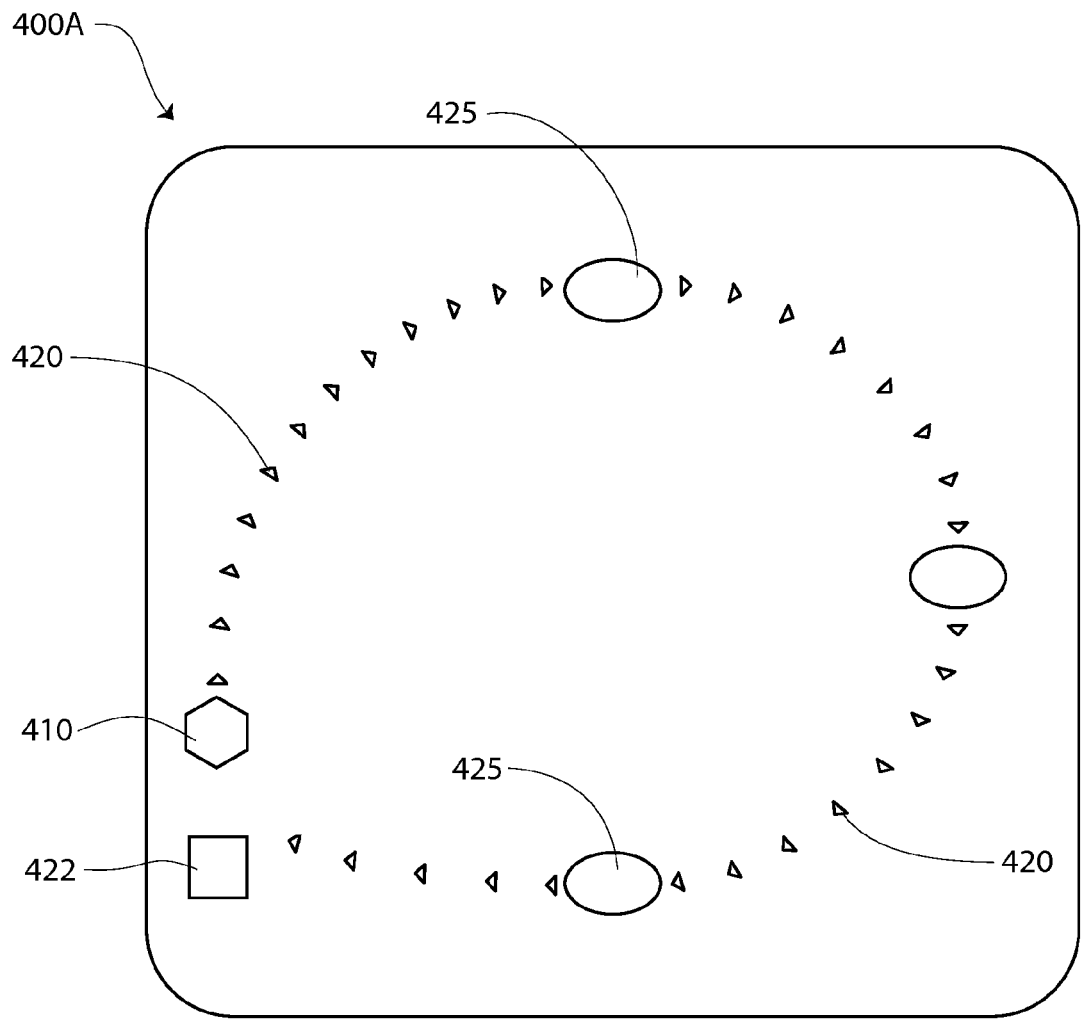
FIGS. 4A-4C present various arrangements for displays from the system of FIG. 1.

As part of therapy, the patient may be asked to move an object over a track or through an obstacle course. FIG. 4A presents a display 400A in a first embodiment. An object 410 is shown ready to be moved over a track 420. The object is moved through lingual manipulation.

The object 410 and the track 420 are indicated as mere geometric shapes. This is certainly an acceptable option. However, it is much preferred that the object 410 and the track 420 present a more interesting subject. For example, the object 410 may be a rabbit or other small animal, and the track 420 may be a garden or area of nature. Alternatively, the object 410 may be a motorcycle or other motorized vehicle, and the track 420 may be a race track, a stunt track or an open road. Alternatively still, the object 410 may be a horse or other racing animal, and the track 420 may be a race track. Other examples include making the object 410 a skateboard, a snowboard, a cartoon character that talks, and so forth. In any instance, the display 400A may include obstacles 425. The obstacles 425 may represent, for example, a fence or a water puddle that is to be jumped.

The display 400A is arranged for the purpose of providing therapy to a patient. However, the system 100 has application to other individuals besides patients undergoing therapy. For example, the system 100 may be used by an individual who is a quadriplegic and must use their intra-oral musculature to move objects. Such an individual may use a wheelchair for mobilization. In that instance, the individual may use the system 100 to operate the wheelchair. Alternatively, such an individual may be bed-ridden and/or unable to fully use their arms. In that instance, the individual may use the system 100 to manipulate the position of the bed.

Figure 4B:
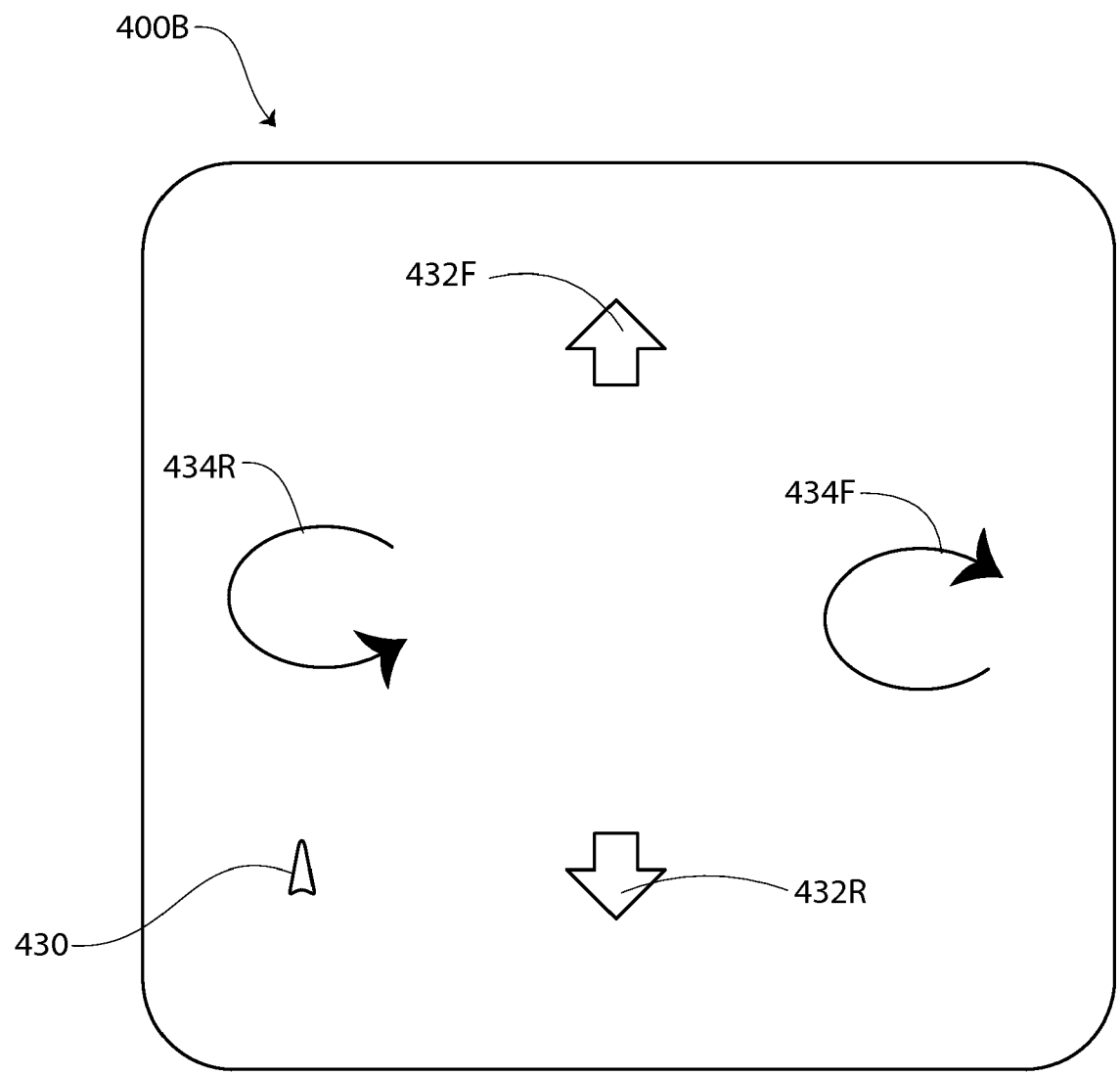

FIG. 4B presents a display 400B for the system 100, in an alternate embodiment. In this system, an object is shown at 430. The object 430 is the object to be moved by the individual through lingual manipulation. In this instance, the object 430 is a cursor or arrow that is moved across the display 400B in accordance with the pressure profile. More specifically, a patient applies pressure to the various air cells in the bulb defining the mouthpiece 110 to ultimately cause translation of the cursor 430 on the display 400B.

The display 400B also includes directional keys. In this arrangement, the directional keys are for moving a wheelchair (not shown). However, the keys may be adapted to move the mattress on a bed frame. The directional keys represent forward 432F and reverse 432R arrows. Actuation of these arrows 432F, 432R causes the wheelchair to move forward or backward. The directional keys also represent clockwise 434F and counter-clockwise 434R arrows. Actuation of these arrows 434F, 434R causes the wheelchair to rotate clockwise or counter-clockwise.

The keys 432F, 432R, 434F, 434R are activated by using the cursor 430. In one aspect, a key 432F, 432R, 434F, or 434R is activated by the user positioning the cursor 430 over the selected key, and then double-clicking on the center air cell 115. In another aspect, a key 432F, 432R, 434F, or 434R is activated by the user positioning the cursor 430 over the selected key, and then pressing against the center air cell 115 for a designated period of time at a certain level of pressure. In the instance where the center air cell 115 is "dead," a key 432F, 432R, 434F, or 434R may be activated by the user positioning the cursor 430 over the selected key, and then pressing against a designated radial air cell 118 or in the center of the mouthpiece 110 for a designated period of time at a certain level of pressure.

The display 400B of FIG. 4B is ideally supported on the individual's wheelchair or bed, as the case may be. For example, the mouthpiece 110 will be mounted on an arm (not shown) that places the mouthpiece 110 in proximity to the user's mouth. In this way, the individual may selectively insert the mouthpiece 110 into their mouth for movement of the wheelchair or bed. In addition, the operational box 142 for the transducers 140 and the processor 150, along with the screen 166, are positioned together on the wheelchair or on the bed. In this instance, the operational box 142 and the processor 150 are an integrated unit.

It is understood in this application that the display 166 will be in electrical communication with a motor or servo-system on the wheelchair or the bed, as the case may be. In this way, the user's instructions delivered by moving the object 430 on the screen 400B cause the wheelchair or bed to respond.

The system 100 may be used by a physically-limited individual to operate other electrical apparatus' besides a wheelchair or a bed. Such apparatus' include, for example, a television, a light fixture, a thermostat or an electro-mechanically operated door. Further, the system 100 may be used to allow the individual to type text messages using just their mouth.

Figure 4C:
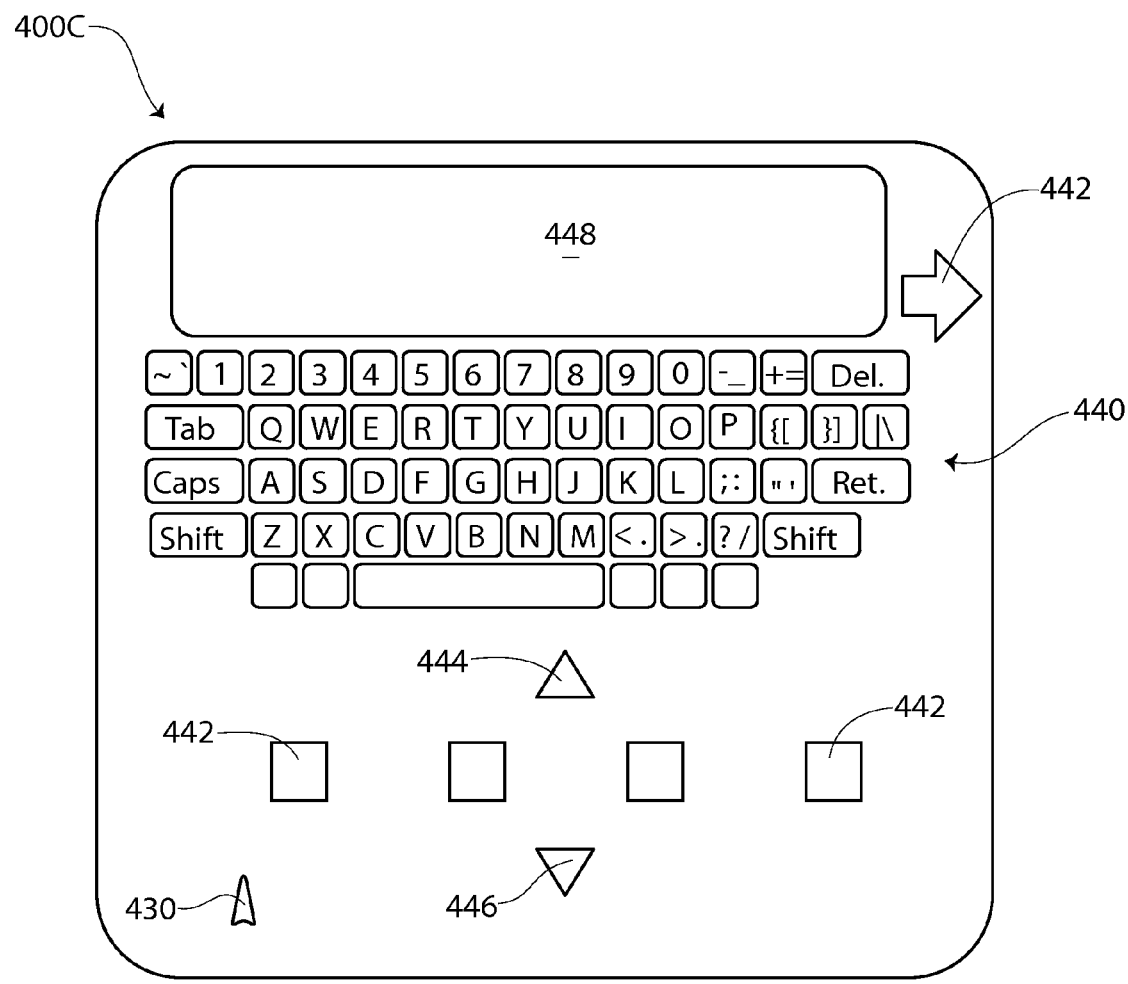

FIG. 4C presents a display 400C for the intra-oral system 100, in an alternate embodiment. In this display 400C, an object is again shown at 430. The object 430 is the object to be moved by the individual through lingual manipulation. The object 430 is again a cursor or arrow that is moved across the display 400C in accordance with the pressure profile.

The display 400C includes icons 442. The icons 442 are pictures that represent various apparatus' as listed above. The individual may select an apparatus to be manipulated by moving the cursor 430 over the corresponding icon 442. The user may then double-click on the center air cell 115 of the mouthpiece 110 to turn the apparatus on or off.

Arrow keys 444, 446 are also provided on the display 400C. The user may further manipulate a selected electrical apparatus by double-clicking on an arrow key 444, 446. For example, a light fixture may be brightened or dimmed by double-clicking on the arrow keys 444, 446. Alternatively, the channel of a television or radio may be changed by double-clicking on the arrow keys 444, 446. Separate arrow keys (not shown) may be used to then adjust the volume.

In lieu of double-clicking, an icon 442 or an arrow key 444, 446 may be selected or activated by the user positioning the cursor 430 over the selected icon 442 or key 444, 446, and then pressing against the center air cell 115 for a designated period of time at a certain level of pressure. In the instance where the center air cell 115 is "dead," a selected icon 442 or key 444, 446 may be activated by the user positioning the cursor 430 over the selected icon 442 key 444, 446, and then pressing against a designated radial air cell 118 or in the centerpoint of the mouthpiece 110 for a designated period of time at a certain level of pressure.

A signal is sent from the system 100 to the electrical apparatus. This signal is preferably a wireless signal such as through infrared technology, Bluetooth technology or other wireless technology that may be known to those of ordinary skill in the art.

The display 400C also includes an optional keyboard 440. The keyboard 440 allows the physically-limited individual to type in a textual message such as an e-mail message to another individual. The individual again uses the cursor 430 to select alpha-numeric keys to be "pressed." Pressing again means double-clicking or otherwise applying pressure to a selected air cell in the mouthpiece 110. By selecting and "pressing" a series of digital keys on the keyboard 440, a message may be composed. The message may be seen on a visualization screen 448 on the display 400C. The message may then be "sent" by pressing a return arrow 442. In this arrangement, the processor has a wired or wireless internet connection for delivering the message through a communications network.

Figure 5:
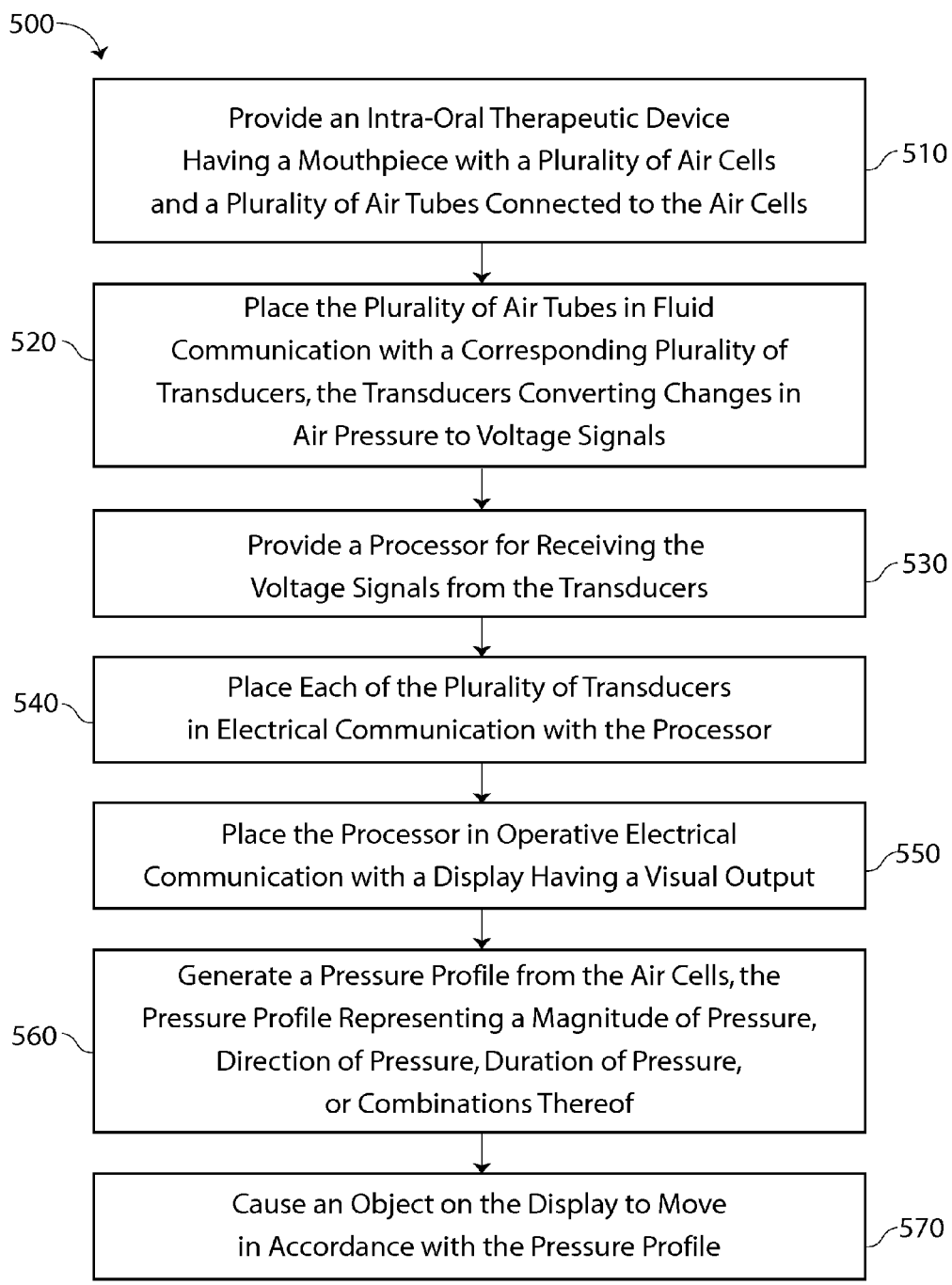
FIG. 5 provides a flowchart for a method for improving intra-oral motor skills of a patient, in one embodiment.

A method for improving intra-oral motor skills of a patient is also provided herein. Improving motor skills will assist the patient in mastication and deglutition. FIG. 5 presents a flow chart, showing steps for generally performing the method 500, in one embodiment.

In accordance with FIG. 5, the method 500 first includes providing an intra-oral device. This is shown in Box 510. The intra-oral device is generally designed as described above in connection with FIGS. 1, 2A-2C, 3, and 4A. In this respect, the device has an elastomeric mouthpiece that defines a bulb. The bulb has a plurality of air cells embedded therein for receiving pressure applied by the tongue of a patient. In one aspect, the mouthpiece comprises at least three outer air cells disposed radially around a centerpoint. The centerpoint may define a separate air cell, or it may be a "dead" area. The cells are divided and sealed by walls.

The intra-oral device also includes a plurality of air tubes. Preferably, each of the plurality of air tubes resides substantially at ambient pressure. Alternatively, each of the plurality of air tubes may be preloaded at a pressure of about 15 psi to 25 psi. This creates desirable additional resistance for more advanced patients. The air tubes preferably have an inner diameter of about 0.05 inches to 0.5 inches. However, other dimensions may be employed.

The distal end of each of the air tubes is in substantially sealed fluid communication with a corresponding air cell. In one aspect, each of the air tubes comprises more than one tubular body operatively connected to form a single, pneumatically sealed channel. In this instance, a manifold may be used to provide a "quick-connect" between sets of air tubes.

The method 500 also includes the step of placing the plurality of air tubes in fluid communication with a corresponding plurality of transducers. To this end, the intra-oral system includes a plurality of transducers. This step is presented in Box 520. The transducers represent pressure sensors that are part of an electrical circuit. The transducers convert changes in air pressure within the air cells to voltage or other electrical signals. The changes in air pressure within the air cells are delivered pneumatically to the transducers through the respective air tubes.

The method 500 also includes the step of providing a processor. The processor receives the voltage signals from the transducers and processes them. This is shown in Box 530.

The method 500 further includes the step of placing each of the plurality of transducers in electrical communication with the processor. This is shown in Box 540. The processor may be placed within the same hardware packaging or box as the transducers. Alternatively, the processor may be a part of a laptop computer or a desktop computer.

The method 500 also includes the step of placing the processor in operative electrical communication with a display. This step is presented in Box 550. To effectuate this step, the intra-oral device also includes a display. The display has a visual output that presents an object.

The method 500 also includes the step of generating a pressure profile from the air cells. This step is provided in Box 560. The pressure profile is generated by the processor in response to the voltage or other electrical signals received from the transducers. The signals are modulated to generate a pressure profile from the air cells. Preferably, the pressure profile represents a magnitude of pressure within the air cells, a direction of pressure, a duration of pressure, or combinations thereof.

The pressure profile is based upon pressure readings from the various air cells. In one aspect, air pressure signals are processed such that each voltage signal represents an air pressure reading from a corresponding air cell. Voltage signals from one or more corresponding air cells are averaged over a specified period of time to produce the pressure profile. The pressure profile has a peak indicative of location at which air pressure is being generated within the one or more air cells during the specified period of time.

The processor sends signals based on pressure profiles to a processing unit. The processing unit is part of a computer system. Signals are sent to the processing unit by means of a USB port or other electronic communications connection. Visualization software is downloaded onto the processing unit to enable the user to see an object being moved on a display.

The method further includes the step of causing an object on the display to move. This is provided at Box 570. The object is moved by means of lingual manipulation of the mouthpiece. More specifically, a patient applies pressure to the various air cells in the mouthpiece to ultimately cause translation of the object on the display.

As part of therapy, the object may be moved through an obstacle course. For example, the object may be a rabbit or other animal, and the course is a race track, a garden or an area of nature. As another example, the object may be a motorized vehicle such as a car or a motorcycle. The motorized vehicle is moved over a track, through simulated city streets, through simulated open roads, or even off road. Other visualization schemes or "games" as described above may be implemented in accordance with graphics software.

In one aspect, a magnitude of each voltage signal is recorded as part of the pressure profile over the specified period of time. The object is then caused to be moved on the display in the direction indicated by the pressure profile at a velocity that corresponds to the magnitude of the voltage signals. In another aspect, an application of pressure by a patient on the centerpoint for a specified period of time and at a specified magnitude causes a location of the object to be reset to a beginning point on the display. Alternatively, an application of pressure by a patient on a designated outer air cell for a specified period of time and at a specified magnitude causes a location of the object to be moved to a corresponding location on the display.

In one aspect, the signal processor receives voltage signals from each of the plurality of transducers. The processor processes the signals such that:

each voltage signal represents an air pressure reading from a corresponding air cell; and voltage signals from one or more corresponding air cells are averaged over a specified period of time to produce the pressure profile, the pressure profile having a peak indicative of location at which air pressure is being generated within the one or more air cells during the specified period of time.

In yet another aspect, an application of pressure by a patient on the centerpoint for a specified period of time and at a specified magnitude causes the object to jump over an obstacle on the display.

The air cells within the mouthpiece may also be configured to respond to double-clicking by the patient. This means that the patient moves his or her tongue against a particular air cell or area of the mouthpiece twice within a designated period of time recognized by the processor. For example, double-clicking of application of pressure by a patient on a centerpoint for a specified period of time and at a specified magnitude may cause a location of the object to be reset to a beginning point on the display, or cause the object to jump over an obstacle on the display.

Figure 6:
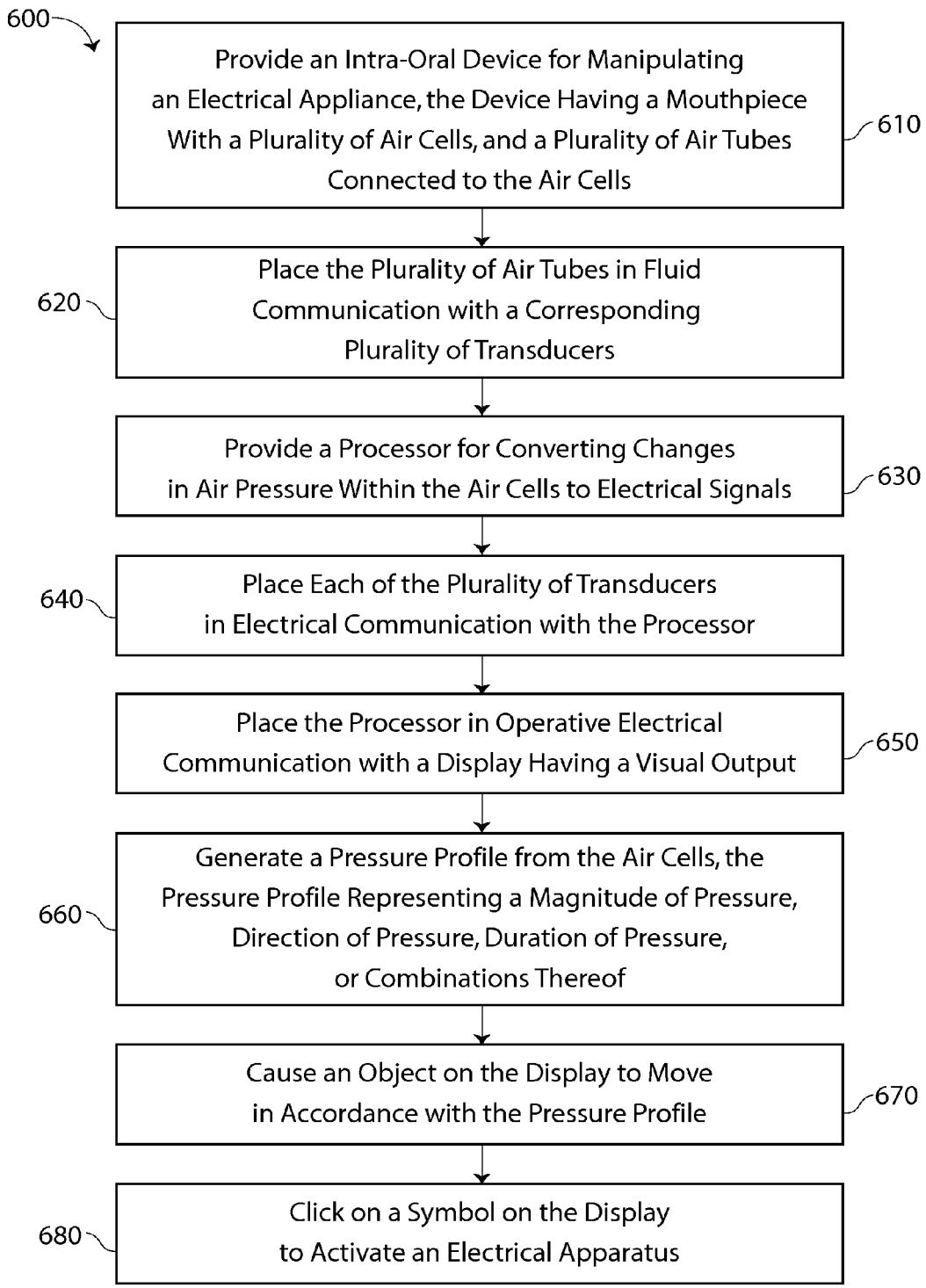
FIG. 6 provides a flowchart for a method for manipulating an object using lingual movement, in one embodiment

A method for manipulating an electrical apparatus using lingual musculature is also provided herein. FIG. 6 presents a flow chart showing steps for generally performing the method 600, in one embodiment.

In accordance with FIG. 6, the method 600 first includes providing an intra-oral device. This is shown in Box 610. The intra-oral device is generally designed as described above in connection with FIGS. 1, 2A, 2B, 2C, 3, 4B and 4C. In this respect, the device has a mouthpiece that defines an elastomeric bulb. The bulb has a plurality of air cells embedded therein for receiving pressure applied by the tongue of a patient. In one aspect, the mouthpiece comprises at least three outer air cells disposed radially around a centerpoint. The centerpoint may define a separate air cell, or it may be a "dead" area.

The intra-oral system also includes a plurality of air tubes. Preferably, each of the plurality of air tubes resides substantially at ambient pressure. The air tubes preferably have an inner diameter of about 0.05 inches to 0.5 inches. However, other dimensions may be employed.

The distal end of each of the air tubes is in substantially sealed fluid communication with a corresponding air cell. In one aspect, each of the air tubes comprises more than one tubular body operatively connected to form a single, pneumatically sealed channel. In this instance, a manifold may be used to provide a "quick-connect" between sets of air tubes.

The method 600 also includes the step of placing the plurality of air tubes in fluid communication with a corresponding plurality of transducers. To this end, the intra-oral system includes a plurality of transducers. This step is presented in Box 620. The transducers represent pressure sensors that are part of an electrical circuit. The transducers convert changes in air pressure within the air cells to electrical signals. The changes in air pressure within the air cells are delivered pneumatically to the transducers through the respective air tubes.

The method 600 also includes the step of providing a processor. The processor receives the electrical signals from the transducers and processes them. This is shown in box 630.

The method 600 further includes the step of placing each of the plurality of transducers in electrical communication with the processor. This is shown in Box 640. Preferably, the processor is placed within the same hardware packaging or box as the transducers. Alternatively, the processor may be a part of a laptop computer or a desktop computer.

The method 600 also includes the step of placing the processor in operative electrical communication with a display. This step is presented in Box 650. To effectuate this step, the intra-oral system also includes a display. The display has a visual output that presents an object.

The method 600 also includes the step of generating a pressure profile from the air cells. This step is provided in Box 660. The pressure profile is generated by the processor in response to the electrical signals received from the transducers. The electrical signals are modulated to generate a pressure profile from the air cells. Preferably, the pressure profile represents a magnitude of pressure within the air cells, a direction of pressure, a duration of pressure, or combinations thereof.

The pressure profile is based upon pressure readings from the various air cells. In one aspect, air pressure signals are processed such that each electrical signal represents an air pressure reading from a corresponding air cell. Electrical signals from one or more corresponding air cells are averaged over a specified period of time to produce the pressure profile. The pressure profile has a peak indicative of location at which air pressure is being generated within the one or more air cells during the specified period of time.

The processor sends signals based on pressure profiles to a processing unit. The processing unit is part of a computer system. Signals are sent to the processing unit by means of a USB port or other electronic communications connection. Visualization software is downloaded onto the processing unit to enable the user to see an object being moved on a display.

The method further includes the step of causing an object on the display to move. This is provided at Box 670. The object is preferably a cursor or arrow that is moved across the display in accordance with the pressure profile. The object is moved over a symbol that represents an electrical apparatus to be activated or a change in the status of an electrical apparatus. The symbol on the display may be of any type. For example, the symbol may be a picture of an electrical apparatus. Alternatively, the symbol may be one or more alphanumeric characters, an arrow indicating direction, or a geometric figure.

In one aspect, a magnitude of each electrical signal is recorded as part of the pressure profile over the specified period of time. The object is then caused to be moved on a display in the direction indicated by the pressure profile at a velocity that corresponds to the magnitude of the electrical signals. In another aspect, an application of pressure by a patient on the centerpoint for a specified period of time and at a specified magnitude causes a location of the object to be reset to a beginning point on the display. Alternatively, an application of pressure by a patient on a designated outer air cell for a specified period of time and at a specified magnitude causes a location of the object to be moved to a corresponding location on the display.

In one aspect, the signal processor receives electrical signals from each of the plurality of transducers. The processor processes the signals such that:

each electrical signal represents an air pressure reading from a corresponding air cell; and electrical signals from one or more corresponding air cells are averaged over a specified period of time to produce the pressure profile, the pressure profile having a peak indicative of location at which air pressure is being generated within the one or more air cells during the specified period of time.

The method 600 further includes the step of clicking on the symbol on the display. Clicking is done through lingual manipulation. This step is shown at Box 680. Using their tongue, a user clicks on a symbol on the display to activate or move an electrical apparatus. The electrical apparatus may be a wheelchair. Alternatively, the electrical apparatus may be, for example, a television, a light fixture or an electro-mechanically operated door.

The above descriptions are not intended to be limiting of scope of the inventions. For example, the present disclosure is not limited to a mouthpiece 110 having the configuration shown in FIGS. 2A-C; other configurations may be employed. The mouthpiece may only have, for instance, two air cells placed in side-by-side relation. The mouthpiece 110 preferably has a handle (not shown).

In another arrangement, the mouthpiece does not use air cells, air tubes and pressure sensors, but instead operates on a system where electrical signals are sent directly from the mouthpiece. The mouthpiece may be arranged in a matrix, with pressure sensors being embedded directly into the mouthpiece within cells defined by the matrix. The pressure sensors may be tactile pressure sensors that detect pressure applied by the patient's tongue as the patient moves his or her tongue across the bottom surface of the bulb. The sensor may measure duration of pressure, direction of pressure, magnitude of pressure, or combinations thereof, at various cell locations.

Each pressure sensor may have its own signature signal. The signature signals are in electrical communication with a first interface. The first interface accumulates pressure data from the various signature signals. This data is then used to create the pressure profile.

In this arrangement, the first interface sends the signature signal data via a communications path. Preferably, the communications path is a wireless communications path directed to a second interface. Thus, as pressure is sensed by a sensor (not shown) in the mouthpiece, the sensor sends a signal to the first interface, which is then communicated to the second interface.

Various types of sensors may be used. For example, a tactile pressure sensor may be used that relies upon resistive-based technology. In this instance the sensor acts as a variable resistor in an electrical circuit. In this application, a small deflection of a matrix in the mouthpiece causes implanted resistors to exhibit a change in ohmic value. The sensor converts this change into a voltage or other electrical signal that is interpreted as a continuous and linear pressure reading. When tactile pressure sensors are unloaded, their resistance is very high. When force is applied, their resistance decreases.

Additional sensing means may be incorporated into each cell in order to sense direction of pressure. In addition, a clock may be associated with each signature signal to measure duration of a detected signal.

Other pressure-sensitive arrangements may be employed. In this respect, the embodiment is not limited by the type of sensor utilized within the cells. For example, a piezo-electric material may be used.

A processor (not shown) is communicably connected with the second interface, such as through a wireless communications system. The processor processes the signature signals to translate location of sensed pressure to a location of an object within a display. The processor may also process the signature signals to translate magnitude of sensed pressure, direction of sensed pressure relative to pressure sensed by at least one other sensor, and the duration of sensed pressure. The processor may manipulate an object within a display, relative to obstacles.

In practice, the patient applies selected pressure to the mouthpiece in order to move an object across a display on a screen. The object is manipulated around a track or over obstacles. The object is moved within the obstacle course in accordance with a pressure profile. The pressure profile comprises at least one parameter defining an operating condition of the mouthpiece. The at least one parameter is selected from the group of parameters consisting of magnitude, direction, duration, and location. For example, the object could be a rabbit, the obstacle course could be a carrot field having fences or rows of vegetation, and the rabbit could pursue carrots between the fences or rows of vegetation which serve as the obstacles.

While it will be apparent that the inventions herein described are well calculated to achieve the benefits and advantages set forth above, it will be appreciated that the inventions are susceptible to modification, variation and change without departing from the spirit thereof.

I claim:

1. An intra-oral system, comprising:
   an elastomeric mouthpiece comprising a bulb, the bulb having a plurality of air cells embedded therein configured to respond to pressure applied by the tongue of an individual;
   a plurality of air tubes, each air tube having a proximal end and a distal end, with the distal end of each of the air tubes being in substantially sealed fluid communication with a corresponding air cell;
   a plurality of transducers for converting changes in air pressure within the air cells to electrical signals, wherein each transducer is in substantially sealed fluid communication with the proximal end of a corresponding air tube;
   a processor for processing the electrical signals, wherein the electrical signals are modulated to generate a pressure profile from the air cells, the pressure profile representing a magnitude of pressure within air cells, a direction of pressure, a duration of pressure, or combinations thereof; and
   a display in operative electrical communication with the processor, the display having a visual output to move an object in accordance with the pressure profile.

2. The intra-oral system of claim 1, wherein the mouthpiece is fabricated from polyisoprene rubber, silicon, chloroprene rubber, neoprene, styrene butadiene rubber, acrylonitrile butadiene rubber, ethylene propylene diene methylene, polyvinylchloride, polyethylene, polyurethane, urethane-coated nylon, ethyl vinyl acetate, and combinations thereof.

3. The intra-oral system of claim 1, wherein the bulb comprises at least three outer air cells disposed radially around a centerpoint.

4. The intra-oral system of claim 3, wherein the centerpoint defines a separate central air cell in fluid communication with one of the plurality of air tubes.

5. The intra-oral therapeutic system of claim 1, wherein:
   each of the plurality of air tubes has an inner diameter of about 0.05 inches to 0.5 inches; and
   each of the plurality of air tubes resides substantially at ambient pressure.

6. The intra-oral system of claim 1, wherein each of the plurality of air tubes is pre-loaded at a pressure of about 15 psi to 25 psi.

7. The intra-oral system of claim 1, wherein:
   the intra-oral system further comprises a manifold; and
   each of the plurality of air tubes comprises more than one tubular body operatively connected to form a single, pneumatically sealed channel by connections to the manifold.

8. The intra-oral system of claim 1, wherein each of the plurality of transducers is a pressure sensor having a diaphragm that is sensitive to changes in pressure within an air tube.

9. The intra-oral system of claim 8, wherein the signal processor receives electrical signals from each of the plurality of transducers and processes those signals such that:

each electrical signal represents an air pressure reading from a corresponding air cell; and electrical signals from one or more corresponding air cells are averaged over a specified period of time to produce the pressure profile, the pressure profile having a peak indicative of location at which air pressure is being generated within the one or more air cells during the specified period of time.

10. The intra-oral system of claim 9, wherein:

a magnitude of each electrical signal is recorded as part of the pressure profile over the specified period of time; and the object is caused to be moved on the display in the direction indicated by the pressure profile.

11. The intra-oral system of claim 10, wherein:

the object is further caused to be moved on the display at a velocity that corresponds to the magnitude of the electrical signals.

12. The intra-oral system of claim 10, wherein the electrical signal is a voltage signal.

13. The intra-oral system of claim 9, wherein the bulb comprises at least three outer air cells disposed radially around a centerpoint.

14. The intra-oral system of claim 13, wherein an application of pressure by a patient on the centerpoint for a specified period of time and at a specified magnitude causes a location of the object to be reset to a beginning point on the display.

15. The intra-oral system of claim 13, wherein an application of pressure by a patient on a designated outer air cell for a specified period of time and at a specified magnitude causes a location of the object to be moved to a corresponding location on the display.

16. The intra-oral system of claim 13, wherein an application of pressure by a patient on the centerpoint for a specified period of time and at a specified magnitude causes the object to jump over an obstacle on the display.

17. The intra-oral system of claim 13, wherein a double-clicking of application of pressure by a patient on the centerpoint for a specified period of time and at a specified magnitude:

causes a location of the object to be reset to a beginning point on the display, causes the object to jump over an obstacle on the display, or causes an electrical apparatus to be activated.

18. The intra-oral system of claim 13, wherein the centerpoint defines a separate air cell in fluid communication with one of the plurality of air tubes.

19. A method for improving oral motor skills of a patient, comprising:

providing an intra-oral therapeutic system, the intra-oral therapeutic system comprising:

an elastomeric mouthpiece comprising a bulb, the bulb having a plurality of air cells embedded therein for receiving pressure applied by the tongue of a patient, a plurality of air tubes, each air tube having a proximal end and a distal end, with the distal end of each of the air tubes being in substantially sealed fluid communication with a corresponding air cell, a plurality of transducers for converting changes in air pressure within the air cells to electrical signals, each transducer being in sealed fluid communication with the proximal end of a corresponding air tube; and a processor for processing the electrical signals, wherein the electrical signals are modulated to generate a pressure profile from the air cells, the pressure profile representing a magnitude of pressure with the air cells, a direction of pressure, a duration of pressure, or combinations thereof;

placing the plurality of air tubes in fluid communication with the corresponding plurality of transducers;

placing the processor in operative electrical communication with a display, the display having a visual output; and by means of lingual manipulation, causing an object on the display to move in accordance with the pressure profile.

20. The method of claim 19, wherein the mouthpiece is fabricated from polyisoprene rubber, silicon, chloroprene rubber, neoprene, styrene butadiene rubber, acrylonitrile butadiene rubber, ethylene propylene diene methylene, polyvinylchloride, polyethylene, polyurethane, urethane-coated nylon, ethyl vinyl acetate, and combinations thereof.

21. The method of claim 19, wherein the bulb comprises at least three outer air cells disposed radially around a centerpoint.

22. The method of claim 21, wherein the centerpoint defines a separate air cell in fluid communication with one of the plurality of air tubes.

23. The method of claim 19, wherein:

each of the plurality of air tubes resides substantially at ambient pressure; and each of the plurality of air tubes has an inner diameter of about 0.05 inches to 0.5 inches.

24. The method of claim 19, wherein each of the plurality of air tubes is pre-loaded at a pressure of about 15 psi to 25 psi.

25. The method of claim 19, wherein each of the plurality of transducers is a pressure sensor having a diaphragm that is sensitive to changes in pressure within an air tube.

26. The method of claim 19, wherein the signal processor receives electrical signals from each of the plurality of transducers and processes those signals such that:

each electrical signal represents an air pressure reading from a corresponding air cell; and electrical signals from one or more corresponding air cells are averaged over a specified period of time to produce the pressure profile, the pressure profile having a peak indicative of location at which air pressure is being generated within the one or more air cells during the specified period of time.

27. The method of claim 26, wherein:

a magnitude of each electrical signal is recorded as part of the pressure profile over the specified period of time; and the object is caused to be moved on the display in the direction indicated by the pressure profile at a velocity that corresponds to the magnitude of the electrical signals.

28. The method of claim 26, wherein the bulb comprises at least three outer air cells disposed radially around a centerpoint.

29. The method of claim 28, wherein an application of pressure by a patient on the centerpoint for a specified period of time and at a specified magnitude causes a location of the object to be reset to a beginning point on the display.

30. The method of claim 28, wherein an application of pressure by a patient on a designated outer air cell for a specified period of time and at a specified magnitude causes a location of the object to be moved to a corresponding location on the display.

31. The method of claim 28, wherein an application of pressure by a patient on the centerpoint for a specified period of time and at a specified magnitude causes the object to jump over an obstacle on the display.

32. The method of claim 28, wherein a double-clicking of application of pressure by a patient on a centerpoint for a specified period of time and at a specified magnitude:
  causes a location of the object to be reset to a beginning point on the display,
  causes the object to jump over an obstacle on the display, or
  causes an electrical apparatus to be activated.

33. The method of claim 28, wherein the centerpoint defines a separate air cell in fluid communication with one of the plurality of air tubes.

34. A method for manipulating an electrical apparatus using lingual musculature, comprising:
  providing an intra-oral system comprising:
    an elastomeric mouthpiece comprising a bulb, the bulb having a plurality of air cells embedded therein for receiving pressure applied by the tongue of a user,
    a plurality of air tubes, each air tube having a proximal end and a distal end, with the distal end of each of the air tubes being in substantially sealed fluid communication with a corresponding air cell,
    a plurality of transducers for converting changes in air pressure within the air cells to electrical signals, each transducer being in sealed fluid communication with the proximal end of a corresponding air tube; and
    a processor for processing the electrical signals, wherein the electrical signals are modulated to generate a pressure profile from the air cells, the pressure profile representing a magnitude of pressure within the air cells, a direction of pressure, a duration of pressure, or combinations thereof;
  placing the plurality of air tubes in fluid communication with the corresponding plurality of transducers;
  placing the processor in operative electrical communication with a display, the display having a visual output;
  causing an object on the display to move in accordance with the pressure profile;
  selecting a symbol on the display; and
  clicking on the symbol on the display.

35. The method of claim 34, wherein the mouthpiece is fabricated from polyisoprene rubber, silicon, chloroprene rubber, neoprene, styrene butadiene rubber, acrylonitrile butadiene rubber, ethylene propylene diene methylene, polyvinylchloride, polyethylene, polyurethane, urethane-coated nylon, ethyl vinyl acetate, and combinations thereof.

36. The method of claim 34, wherein the bulb comprises at least three outer air cells disposed radially around a centerpoint.

37. The method of claim 36, wherein the centerpoint defines a separate air cell in fluid communication with one of the plurality of air tubes.

38. The method of claim 36, wherein:
  each of the plurality of air tubes resides substantially at ambient pressure; and
  each of the plurality of air tubes has an inner diameter of about 0.05 inches to 0.5 inches.

39. The method of claim 36, wherein the symbol on the display comprises a picture, one or more alphanumeric characters, an arrow, or a geometric figure.

40. The method of claim 34, wherein each of the plurality of transducers is a pressure sensor having a diaphragm that is sensitive to changes in pressure within an air tube.

41. The method of claim 34, wherein the signal processor receives voltage signals from each of the plurality of transducers and processes those signals such that:
  each voltage signal represents an air pressure reading from a corresponding air cell; and
  voltage signals from one or more corresponding air cells are averaged over a specified period of time to produce the pressure profile, the pressure profile having a peak indicative of location at which air pressure is being generated within the one or more air cells during the specified period of time.

42. The method of claim 34, wherein the electrical apparatus is a wheelchair, a light fixture, a television, or an electromechanically operated door.

43. The method of claim 34, wherein the bulb comprises at least three outer air cells disposed radially around a centerpoint.

44. The method of claim 43, wherein an application of pressure by a patient on the centerpoint for a specified period of time and at a specified magnitude causes a location of the object to be reset to a beginning point on the display.

45. The method of claim 43, wherein an application of pressure by a patient on a designated outer air cell for a specified period of time and at a specified magnitude causes a location of the object to be moved to a corresponding location on the display.

46. The method of claim 43, wherein clicking on a symbol on the display constitutes a double-clicking of application of pressure by a patient on a centerpoint for a specified period of time and at a specified magnitude.

47. The method of claim 43, wherein the centerpoint defines a separate air cell in fluid communication with one of the plurality of air tubes.

48. The method of claim 43, wherein:
  the display further comprises a keyboard;
  selecting a symbol on the display comprises selecting a series of characters on the keyboard; and
  clicking on the symbol on the display comprises composing a textual message.

49. The method of claim 48, further comprising:
  sending the textual message through a wireless communications system.

50. The method of claim 43, wherein:
  selecting a symbol on the display comprises selecting a directional key; and
  clicking on the symbol on the display causes a wheelchair or a bed to move.

51. The method of claim 43, wherein:
  selecting a symbol on the display comprises selecting an icon representing an electrical apparatus; and
  clicking on the symbol on the display causes the apparatus to be turned on or turned off.

52. The method of claim 51, further comprising:
  selecting a symbol on the display further comprises selecting a directional key; and
  clicking on the symbol on the display causes a condition of the apparatus to be changed.

53. The method of claim 52, wherein the electrical apparatus is a light fixture, a television, a radio, or a mechanically operated door.

* * * * *